(12) United States Patent
Bohnert et al.

(10) Patent No.: US 12,090,242 B2
(45) Date of Patent: Sep. 17, 2024

(54) METHODS AND DEVICES FOR STERILIZING MEDICAL EQUIPMENT

(71) Applicant: Honeywell Federal Manufacturing & Technologies, LLC, Kansas City, MO (US)

(72) Inventors: George William Bohnert, Kansas City, MO (US); Darren Radke, Kansas City, MO (US); Domenick Leto, Kansas City, MO (US)

(73) Assignee: Honeywell Federal Manufacturing & Technologies, LLC, Kansas City, MO (US)

( * ) Notice: Subject to any disclaimer, the term of this patent is extended or adjusted under 35 U.S.C. 154(b) by 0 days.

(21) Appl. No.: 18/140,881

(22) Filed: Apr. 28, 2023

(65) Prior Publication Data

US 2023/0270903 A1 Aug. 31, 2023

Related U.S. Application Data

(62) Division of application No. 17/011,601, filed on Sep. 3, 2020, now Pat. No. 11,672,880.

(60) Provisional application No. 63/012,580, filed on Apr. 20, 2020.

(51) Int. Cl.
*A61L 2/20* (2006.01)
(52) U.S. Cl.
CPC ......... *A61L 2/208* (2013.01); *A61L 2202/122* (2013.01); *A61L 2202/181* (2013.01); *A61L 2202/24* (2013.01)

(58) Field of Classification Search
None
See application file for complete search history.

(56) References Cited

U.S. PATENT DOCUMENTS

| | | | | |
|---|---|---|---|---|
| 3,476,506 A | * | 11/1969 | Andersen | A61L 2/206 |
| | | | | 422/294 |
| 9,592,310 B1 | * | 3/2017 | Hughes | A61L 9/12 |
| 2002/0168289 A1 | * | 11/2002 | McVey | A61L 2/208 |
| | | | | 422/108 |
| 2015/0328259 A1 | * | 11/2015 | Shanler | A61K 9/08 |
| | | | | 604/290 |
| 2017/0217661 A1 | * | 8/2017 | Erickson | A61L 2/208 |

(Continued)

OTHER PUBLICATIONS

Maunu et al., Vaporized Hydrogen Peroxide (H2O2) Vs. Vaporized Ethylene Oxide (EtO), Jan. 21, 2019, blog post published at URL <https://www.vaisala.com/en/blog/2022-12/vaporized-hydrogen-peroxide-h2o2-vs-vaporized-ethylene-oxide-eto> (Year: 2019).*

*Primary Examiner* — Holly Kipouros
(74) *Attorney, Agent, or Firm* — Hovey Williams LLP (57) ABSTRACT

A hydrogen peroxide sterilization device for sterilizing a medical device, the hydrogen peroxide sterilization device including a hermetic outer container, a hydrogen peroxide pouch, and a hydrogen peroxide solution in the solution chamber. The hermetic outer container includes a sterilization enclosure configured to receive the medical device. The hydrogen peroxide pouch includes a permeable membrane enclosing a solution chamber and is configured to be positioned in the sterilization enclosure of the outer container. The permeable membrane is configured to allow hydrogen peroxide vapor to diffuse from the solution chamber through the permeable membrane into the sterilization enclosure.

12 Claims, 2 Drawing Sheets

(56) References Cited

U.S. PATENT DOCUMENTS

2019/0247137 A1* 8/2019 Gallagher ............. B65B 7/2878
2021/0138449 A1* 5/2021 Hinkle ...................... F24F 7/06

* cited by examiner

METHODS AND DEVICES FOR STERILIZING MEDICAL EQUIPMENT

GOVERNMENT INTERESTS

This invention was made with Government support under Contract No.: DE-NA-0002839 awarded by the United States Department of Energy/National Nuclear Security Administration. The Government has certain rights in the invention.

RELATED APPLICATIONS

This application is a regular utility non-provisional patent application, and claims priority benefit with regard to all common subject matter, of U.S. Non-Provisional patent application Ser. No. 17/011,601, entitled "METHODS AND DEVICES FOR STERILIZING MEDICAL EQUIPMENT", and filed Sep. 3, 2020. Application Ser. No. 17/011,601 claims priority benefit of U.S. Provisional Patent Application Ser. No. 63/012,580, entitled "METHODS AND DEVICES FOR STERILIZING MEDICAL EQUIPMENT", and filed Apr. 20, 2020. The above-mentioned previously filed applications are hereby incorporated by reference in their entireties into the present application.

BACKGROUND

Hydrogen peroxide is often used for sterilizing medical equipment, electronics, work surfaces, and common areas, but aqueous hydrogen peroxide solutions are undesirable because they require a sterilized device or surface to be dried before use. Industrial machines are used to convert hydrogen peroxide liquid into droplets, mist, and vapor for sterilizing large volumes such as cargo containers, hospital rooms, and office buildings, but that approach is not viable for sterilizing medical devices in emergencies, in remote or isolated locations, during travel, or in one-off situations.

SUMMARY

Embodiments of the invention solve the above-mentioned problems and other problems and provide a distinct advancement in the art of medical equipment sterilization. More particularly, the invention provides devices and methods for sterilizing medical equipment via controlled hydrogen peroxide vapor delivery.

An embodiment of the invention is a hydrogen peroxide sterilization device broadly comprising a hermetic outer container, a hydrogen peroxide pouch, an indicator, and a desiccant pouch. The hydrogen peroxide sterilization device is described in terms of sterilizing a medical face mask, but other medical devices, tools, and equipment may also be sterilized.

The hermetic outer container includes an outer wall and an opening sealing mechanism. The hermetic outer container may be molded to fit the item being sterilized (similar to clamshell packaging) to reduce the amount of hydrogen peroxide vapor required to fill the space around the item.

The outer wall forms a sterilization enclosure having an opening and retains water vapor and hydrogen peroxide vapor in the sterilization enclosure. To that end, the outer wall may be polyethylene, polypropylene, metal, fluoropolymers (perfluoroalkoxy alkanes (PFA), fluorinated ethylene propylene (FEP), etc. or any other suitable hermetic material.

The opening allows the user to insert the face mask and the hydrogen peroxide pouch into the sterilization enclosure. The opening may be closed via the opening sealing mechanism.

The opening sealing mechanism is configured to be selectively opened for inserting the face mask into and removing the face mask from the sterilization enclosure. The opening sealing mechanism seals the sterilization enclosure when the opening sealing mechanism is closed. The opening sealing mechanism may be a zip-to-close mechanism, a press-and-seal mechanism, or any other suitable hermetic sealing mechanism.

The hydrogen peroxide pouch comprises a permeable membrane and a hermetic liner and forms a solution chamber. The hydrogen peroxide pouch is configured to be inserted into the sterilization enclosure with the face mask. In one embodiment, the hydrogen peroxide pouch is formed by heat sealing open sides of material. The solution chamber receives hydrogen peroxide solution and may be 0.2 milliliters or any other suitable volume. The solution chamber may be sealed or may be refillable and resealable.

The permeable membrane encloses the solution chamber and may be spun bonded polyethylene or any other suitable material configured to allow hydrogen peroxide vapor to diffuse out of the solution chamber into the sterilization enclosure. The permeable membrane may be heat sealed.

The hermetic liner encloses the permeable membrane and may be a plastic-lined metal pouch. For example, the hermetic liner may be a thin flexible plastic-lined foil. The hermetic liner is configured to prevent the hydrogen peroxide vapor from diffusing out of the solution chamber into the sterilization enclosure unless the hermetic outer liner is compromised via cutting, puncturing, tearing, or the like.

The hydrogen peroxide solution is a mixture of water and hydrogen peroxide. Hydrogen peroxide concentration may be between 1% and 100% (pure hydrogen peroxide with no water). In one embodiment, inhibited hydrogen peroxide may be ACS reagent grade, between 10% and 35% (by weight).

The indicator reacts to hydrogen peroxide and identifies a concentration or amount of hydrogen peroxide in the sterilization enclosure and/or the solution chamber. To that end, the indicator may be located in the sterilization enclosure (e.g., on an inner surface of the hermetic outer container).

The desiccant pouch comprises a permeable membrane that includes activated 3 Å molecular sieves (desiccant) to control humidity within the sterilization enclosure. The molecular sieves lower the water vapor concentration within the sterilization enclosure, thus allowing more hydrogen peroxide to enter the sterilization enclosure. The desiccant pouch is sealed in a hermetic liner to increase shelf-life. The hermetic liner encloses the permeable membrane and may be a plastic-lined metal pouch. For example, the hermetic liner may be a thin flexible plastic-lined foil. The hermetic liner is configured to prevent the desiccant from absorbing water vapor unless the hermetic outer liner is compromised via cutting, puncturing, tearing, or the like.

In use, the face mask is placed in the sterilization enclosure of the hermetic outer container via its opening. The hermetic liner of the hydrogen peroxide pouch is then cut, torn, punctured, or at least partially removed. The hydrogen peroxide pouch is then placed in the sterilization enclosure with the face mask. The hermetic liner of the desiccant pouch is then cut, torn, punctured, or at least partially removed. The desiccant pouch is then placed in the sterilization enclosure with the face mask. The opening sealing mechanism is then closed so that no vapor can diffuse out of the sterilization enclosure.

At least some of the hydrogen peroxide in the hydrogen peroxide solution then diffuses through the permeable membrane in the form of vapor into the sterilization enclosure and sterilizes the face mask. To that end, the face mask and the hydrogen peroxide pouch may be retained in the sterilization enclosure for a predetermined or recommended amount of time, until the face mask is needed again, until the hydrogen peroxide solution has completely diffused into the sterilization enclosure, or until the indicator indicates a particular amount of hydrogen peroxide solution has diffused into the sterilization enclosure.

The opening sealing mechanism is then opened, and the face mask is removed from the hermetic outer container. The hydrogen peroxide pouch may be discarded, refilled and resealed for future use, or reused if some of the hydrogen peroxide solution remains. To that end, the hydrogen peroxide pouch may be stored in the hermetic outer container until the hydrogen peroxide sterilization device is used again.

The above-described hydrogen peroxide sterilization device provides several advantages. For example, the hydrogen peroxide pouch can be sized to fit a large variety of enclosures and to accommodate a large range of sterilization loads. Only a small quantity of hydrogen peroxide is needed for individual medical device sterilization, making the hydrogen peroxide sterilization device safe to use without training. Hydrogen peroxide concentrations can be adjusted to optimize sterilization and safety. The hydrogen peroxide pouch may be reusable depending on the hydrogen peroxide concentration and active diffusion time. In some embodiments, the hydrogen peroxide pouch is resealable. Off-the-shelf hermetic outer containers such as polyethylene bags can be used.

Another embodiment of the invention is a hydrogen peroxide sterilization device broadly comprising a hermetic outer container and a hydrogen peroxide ampoule. The hydrogen peroxide sterilization device is similar to the hydrogen peroxide device described above except instead of a hydrogen peroxide pouch, the hydrogen peroxide ampoule delivers hydrogen peroxide vapor into the sterilization enclosure of the hermetic outer container.

The hydrogen peroxide ampoule comprises a glass tube and a permeable membrane and forms a solution chamber. The hydrogen peroxide ampoule is configured to be inserted into the sterilization enclosure with the medical device. An open ended plastic sleeve covering the ampoule protects the membrane from cutting when the ampoule is crushed. The hydrogen peroxide ampoule may provide longer hydrogen peroxide shelf life.

The glass tube is a hermetic vessel that encloses the solution chamber and hence retains hydrogen peroxide solution in the solution chamber. The glass tube may be shattered or broken when sterilization is desired.

The permeable membrane encloses the glass tube and may be spun bonded polyethylene or any other suitable material configured to allow hydrogen peroxide vapor to diffuse into the sterilization enclosure. The permeable membrane may be heat sealed.

In use, the face mask may be placed in the sterilization enclosure of the hermetic outer container via its opening. The hydrogen peroxide ampoule may then be placed in the sterilization enclosure with the face mask. The hermetic liner of the desiccant pouch is then cut, torn, punctured, or at least partially removed. The desiccant pouch is then placed in the sterilization enclosure with the face mask. The opening sealing mechanism may then be closed so that no vapor can diffuse out of the sterilization enclosure. The glass tube of the hydrogen peroxide ampoule may then be shattered or broken.

At least some of the hydrogen peroxide in the hydrogen peroxide solution then diffuses through the permeable membrane in the form of vapor into the sterilization enclosure and sterilize the face mask. To that end, the face mask and the hydrogen peroxide ampoule may be retained in the sterilization enclosure for a predetermined or recommended amount of time, until the face mask is needed again, or until the hydrogen peroxide solution has completely diffused into the sterilization enclosure.

The opening sealing mechanism may then be opened, and the face mask may then be removed from the hermetic outer container. The hydrogen peroxide ampoule may then be discarded.

Another embodiment of the invention is a hydrogen peroxide sterilization device broadly comprising a hermetic outer container and a hydrogen peroxide receptacle. The hydrogen peroxide sterilization device is similar to the hydrogen peroxide devices described above except instead of a hydrogen peroxide pouch or a hydrogen peroxide ampoule, the hydrogen peroxide receptacle delivers hydrogen peroxide vapor into the sterilization enclosure of the hermetic outer container.

The hydrogen peroxide receptacle includes a hermetic base vessel, a permeable lid, and a hermetic lid. The hydrogen peroxide receptacle may be a closable bottle, a vile, a capsule, or any other suitable rigid receptacle.

The hermetic base vessel is a rigid or minimally flexible container forming a solution chamber. The hermetic base vessel may be made of plastic, glass, ceramic, metal, or the like.

The permeable lid includes a permeable membrane and is configured to be removably secured onto the hermetic base vessel to fully enclose the solution chamber. To that end, the permeable lid may be snapped or crimped onto the hermetic base vessel or attached to the hermetic base vessel via a fastener. Alternatively, the permeable lid (and/or hermetic base vessel) may include helical threads for screwing the permeable lid on to the hermetic base vessel.

The permeable membrane may be spun bonded polyethylene or any other suitable material configured to allow hydrogen peroxide vapor to diffuse out of the solution chamber. The permeable membrane may be heat sealed.

The hermetic lid is configured to be removably secured onto the permeable lid or onto the hermetic base vessel over the permeable lid. To that end, the hermetic lid may be snapped or crimped onto the permeable lid or hermetic base vessel or attached to the permeable lid or hermetic base vessel via a fastener. Alternatively, the hermetic lid may include helical threads for screwing the hermetic lid onto the permeable lid or hermetic base vessel.

In use, a face mask may be placed in the sterilization enclosure of the hermetic outer container via its opening. The hermetic lid and the permeable lid may then be removed from the hermetic base vessel. A hydrogen peroxide solution may then be poured into the hermetic base vessel. The permeable lid may then be secured onto the hermetic base vessel, thus sealing the hydrogen peroxide solution in the solution chamber. The hydrogen peroxide receptacle may then be placed in the sterilization enclosure with the medical device. The opening sealing mechanism of the hermetic outer container may then be closed so that no vapor can diffuse out of the sterilization enclosure At least some of the hydrogen peroxide in the hydrogen peroxide solution then diffuses through the permeable membrane in the form of vapor into the sterilization enclosure and sterilize the medical device. To that end, the medical device and the hydrogen peroxide receptacle may be retained in the sterilization enclosure for a predetermined or recommended amount of time (depending on the medical device or its application), until the medical device is needed again, until the hydrogen peroxide solution has completely diffused into the sterilization enclosure, or until the indicator indicates a particular amount of hydrogen peroxide solution has diffused into the sterilization enclosure.

The opening sealing mechanism may then be opened, and the medical device may then be removed from the hermetic outer container. The hydrogen peroxide receptacle may be discarded, refilled and resealed for future use, or reused if some of the hydrogen peroxide solution remains. To that end, the hydrogen peroxide receptacle may be stored in the hermetic outer container until the hydrogen peroxide sterilization device is used again.

BRIEF DESCRIPTION OF THE DRAWING FIGURES

Embodiments of the present invention are described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
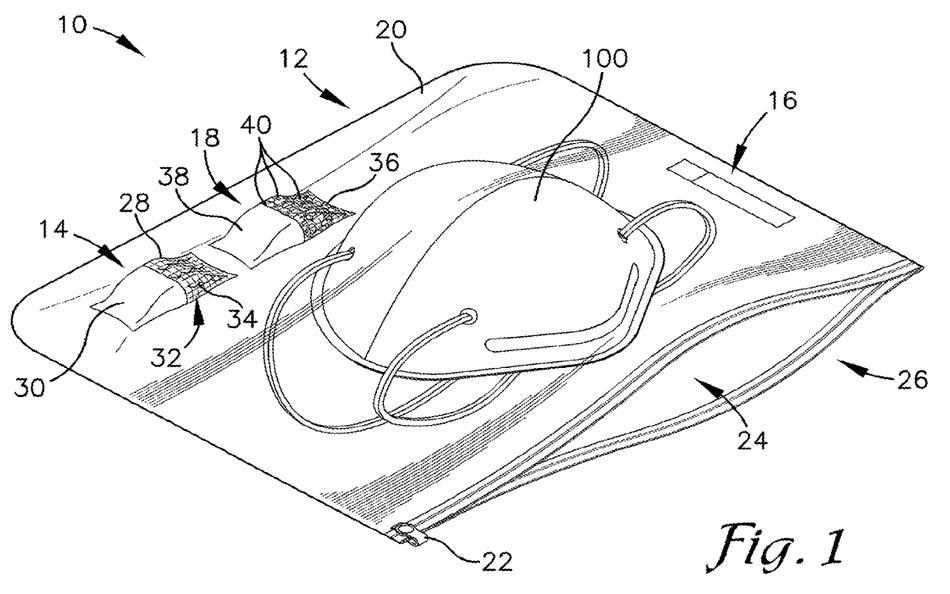
FIG. 1 is a perspective view of a hydrogen peroxide sterilization device constructed in accordance with an embodiment of the invention.

Turning to FIG. 1, a hydrogen peroxide sterilization device 10 for sterilizing a medical device is illustrated. The hydrogen peroxide sterilization device 10 broadly comprises a hermetic outer container 12, a hydrogen peroxide pouch 14, an indicator 16, and a desiccant pouch 18. The hydrogen peroxide sterilization device 10 is shown sterilizing an exemplary medical device 100, which may be a face mask or any other medical tool or personal health device.

The hermetic outer container 12 includes an outer wall 20 and an opening sealing mechanism 22. The hermetic outer container 12 may be molded to fit the item being sterilized (similar to clamshell packaging) to reduce the amount of hydrogen peroxide vapor required to fill the space around the item. The hermetic outer container 12 may be a polyethylene bag, a polypropylene bag, or any other suitable hermetic container. High density polyethylene provides an acceptable vapor barrier, whereas low density polyethylene may be a poor barrier to oxygen and hydrogen peroxide.

The outer wall 20 forms a sterilization enclosure 24 having an opening 26 and retains water vapor and hydrogen peroxide vapor in the sterilization enclosure 24. To that end, the outer wall 20 may be polyethylene, polypropylene, or any other suitable hermetic material. The outer wall 20 may be transparent, thus allowing a user to observe the medical device 100 or personal health device without opening the hermetic outer container 12. The outer wall 20 may be flexible for altering a volume of the sterilization enclosure 24.

The sterilization enclosure 24 receives the medical device 100 or personal health device and the hydrogen peroxide pouch 14 therein. The sterilization enclosure 24 may be approximately one liter in maximum volume or any other suitable size.

The opening 26 allows the user to insert the medical device 100 or personal health device and the hydrogen peroxide pouch 14 into the sterilization enclosure 24. The opening 26 may be closed via the opening sealing mechanism 22.

The opening sealing mechanism 22 is configured to be selectively opened for inserting the medical device 100 or personal health device into and removing the medical device 100 or personal health device from the sterilization enclosure 24. The opening sealing mechanism 22 seals the sterilization enclosure 24 when the opening sealing mechanism 22 is closed. The opening sealing mechanism 22 may be a zip-to-close mechanism, a press-and-seal mechanism, or any other suitable hermetic sealing mechanism.

The hydrogen peroxide pouch 14 comprises a permeable membrane 28 and a hermetic liner 30 and forms a solution chamber 32. The hydrogen peroxide pouch 14 is configured to be inserted into the sterilization enclosure 24 with the medical device 100 or personal health device. The hydrogen peroxide pouch 14 may be rectangular or any other suitable shape. In one embodiment, the hydrogen peroxide pouch 14 is formed by heat sealing open sides of material. For example, a Midwest Pacific Impulse Heat Sealer model MP-12 set on 3.8 may effectively heat seal the hydrogen peroxide pouch 14. The hydrogen peroxide pouch 14 may have an area of 100 $cm^2$ or any other suitable area. The solution chamber 32 receives hydrogen peroxide solution 34 and may be 0.2 milliliters or any other suitable volume. The solution chamber 32 may be sealed or may be refillable and resealable.

The permeable membrane 28 encloses the solution chamber 32 and may be spun bonded polyethylene, such as Tyvek brand, or any other porous material, such as Gore-Tex brand, configured to allow hydrogen peroxide vapor to diffuse out of the solution chamber 32 into the sterilization enclosure 24. The permeable membrane 28 may be heat sealed. The permeable membrane 28 may be transparent, thus allowing a user to observe an amount of hydrogen peroxide solution 34 in the hydrogen peroxide pouch 14.

In one embodiment, the permeable membrane 28 may be 0.006 inches thick and made from 50 gram/meter$^2$ spun bonded polyethylene fabric. Good transport of hydrogen peroxide vapor occurs as the fabric is approximately two-thirds void space, since 0.006 inch thick solid polyethylene film weighs 141 gram/meter$^2$. The high surface area of the fabric also allows for more efficient vaporization of hydrogen peroxide. Other spun bonded fabrics such as polypropylene or polyester having a similar void volume may also be used.

The hermetic liner 30 encloses the permeable membrane 28 and may be a plastic-lined metal pouch. For example, the hermetic liner 30 may be a thin flexible plastic-lined foil, to allow for it to be heat sealed. The hermetic liner 30 is configured to prevent the hydrogen peroxide vapor from diffusing out of the solution chamber 32 into the sterilization enclosure 24 unless the hermetic outer liner 30 is compromised via cutting, puncturing, tearing, or the like. To that end, the hermetic liner 30 may have a crease, crimp line, or notch for facilitating a compromising action.

The hydrogen peroxide solution 34 may be a mixture of water and hydrogen peroxide, such as the inhibited hydrogen peroxide solution supplied by Sigma Aldrich. Hydrogen peroxide concentration may be between 1% and 100% (pure hydrogen peroxide with no water). In one embodiment, hydrogen peroxide may be ACS reagent grade, between 10% and 35% (by weight). In another embodiment, ACS reagent grade, 30% (by weight) hydrogen peroxide solution may be used. The hydrogen peroxide solution 34 may be between approximately 100 milliliters to approximately 500 milliliters. For extended shelf life, the hydrogen peroxide solution 34 may be packaged in glass ampoules within the hydrogen peroxide pouch 14 and broken when ready for use. The hydrogen peroxide solution 34 may be shipped in a bottle made of high-density polyethylene.

The indicator 16 reacts to hydrogen peroxide and identifies a concentration or amount of hydrogen peroxide in the sterilization enclosure 24 and/or the solution chamber 32. The indicator 16 may be an indicator strip such as an XploSens PS. In one embodiment, the indicator 16 has a range of 0-500 ppm and turns orange when exposed to saturated water/hydrogen peroxide vapor at room temperature. The indicator 16 may be located in the sterilization enclosure 24 (e.g., on an inner surface of the hermetic outer container 12). In other words, the indicator 16 may be located anywhere that alerts a user to an amount of vapor diffusion in the hydrogen peroxide pouch 14. If more precise hydrogen peroxide concentration monitoring is required, a probe such as a Vaisala HPP272 hydrogen peroxide, humidity, and temperature probe may be used. Detection range of the above probe is 0 ppm to 2,000 ppm.

The desiccant pouch 18 includes a permeable membrane 36 and a hermetic liner 38 and holds activated 3 Å molecular sieves 40 (desiccant) to control humidity within the sterilization enclosure 24. The molecular sieves 40 lower the water vapor concentration within the sterilization enclosure 24, thus allowing more hydrogen peroxide to enter the sterilization enclosure 24. Without the desiccant, the water and hydrogen peroxide vapor quickly saturate the air in the sterilization enclosure 24, thus preventing further vaporization of water and hydrogen peroxide. Hydrogen peroxide molecules are slightly larger than water molecules, resulting in the preferential uptake of water molecules by the desiccant. In one embodiment, 6 grams of desiccant may be used. The desiccant pouch 18 may be a spun bonded polyethylene pouch with a metal foil outer packaging to prevent moisture uptake until needed.

The permeable membrane 36 encloses the molecular sieves 40 and may be spun bonded polyethylene or any other suitable material configured to allow water vapor to pass into the desiccant pouch 18 and be absorbed by the molecular sieves 40. The permeable membrane 36 may be heat sealed.

The hermetic liner 38 encloses the permeable membrane 36 and may be a thin flexible plastic-lined metal foil. The hermetic liner 38 prevents the molecular sieves 40 from absorbing water unless the hermetic liner 38 is compromised via cutting, puncturing, tearing, or the like. As such, the hermetic liner 38 increases shelf life of the molecular sieves 40.

Use of the hydrogen peroxide sterilization device 10 will now be described. First, the medical device 100 or personal health device may be placed in the sterilization enclosure 24 of the hermetic outer container 12 via its opening 26. The hermetic liner 30 of the hydrogen peroxide pouch 14 may then be cut, torn, punctured, or at least partially removed. The hermetic liner 38 of the desiccant pouch 18 may also be cut, torn, punctured, or at least partially removed. The hydrogen peroxide pouch 14 and desiccant pouch 18 may then be placed in the sterilization enclosure 24 with the medical device 100 or personal health device. The opening sealing mechanism 22 may then be closed so that no vapor can diffuse out of the sterilization enclosure 24. In one embodiment, a dry gas may be added to the sterilization enclosure 24 before it is closed to increase the diffusion of hydrogen peroxide vapor through the permeable membrane 28.

At least some of the hydrogen peroxide in the hydrogen peroxide solution 34 will then diffuse through the permeable membrane 28 in the form of vapor into the sterilization enclosure 24 and sterilize the medical device 100 or personal health device. To that end, the medical device 100 or personal health device and the hydrogen peroxide pouch 14 may be retained in the sterilization enclosure 24 for a predetermined or recommended amount of time (depending on the medical device 100 or personal health device or its application), until the medical device 100 or personal health device is needed again, until the hydrogen peroxide solution 34 has completely diffused into the sterilization enclosure 24, or until the indicator indicates a particular amount of hydrogen peroxide solution 34 has diffused into the sterilization enclosure 24.

The opening sealing mechanism 22 may then be opened, and the medical device 100 or personal health device may then be removed from the hermetic outer container 12. The hydrogen peroxide pouch 14 may be discarded, refilled and resealed for future use, or reused if some of the hydrogen peroxide solution 34 remains. To that end, the hydrogen peroxide pouch 14 may be stored in the hermetic outer container 12 until the hydrogen peroxide sterilization device 10 is used again.

A test of the above concepts was performed via 1.0 liter Nalgene high density polyethylene bottles, which showed significantly higher concentrations of hydrogen peroxide vapor than low density polyethylene bags. In addition to being made of HDPE, the Nalgene bottle is much thicker at 0.060 inches compared to 0.0015 inches for an LLDPE bag. Since hydrogen peroxide vapor containment is an important aspect of the invention, materials having low oxygen transmission rates are desirable. Examples include aluminum foil, metalized polyester, perfluoroalkoxy alkanes (PFA), fluorinated ethylene propylene (FEP), metalized polyethylene terephthalate (Mylar), ethylene vinyl alcohol (EVOH), and polyvinylidene chloride.

Similarly, ½ gallon and 1 gallon HDPE Nalgene bottles were evaluated, with maximum hydrogen peroxide concentration shown in Table 1 below. Each containment vessel held two Du Pont Sierra masks, size 7 inch, Part number ML 7330BU000500BH, and 6 grams of 3 Å molecular sieves. Maximum hydrogen peroxide vapor concentrations were achieved within 6 hours to 8 hours after start of the test and gradually declined to zero over a 24 hour period.

TABLE 1

| Vessel size | Material | HP loading μ liters | PPM | RS (%) (1) |
|---|---|---|---|---|
| 1 gal bag | LLDPE | 250 | 211 | 8.1 |
| 1 gal bag (2) | LLDPE | 300 | 96 | 71.9 |
| 1 liter bottle | HDPE | 250 | 945 | 23.9 |
| 1 liter bottle (3) | HDPE | 250 | 1292 | 65.9 |
| 1 liter bottle | HDPE | 300 | 1004 | 80.4 |
| 1 liter bottle | HDPE | 300 | 1045 | 87.4 |
| ½ gal bottle | HDPE | 300 | 928 | 34.2 |
| ½ gal bottle | HDPE | 300 | 822 | 34.4 |
| 1 gal bottle | HDPE | 500 | 670 | 62.1 |
| 1 gal bottle | HDPE | 500 | 724 | 58.3 |
| 1 gal bag | FEP | 400 | 698 | 56.5 |
| ½ gal bag | PET metalized | 300 | 528 | 44.7 |
| ½ gal bag | PFA | 400 | 558 | 26.9 |

(1) Relative Saturation (RS)-indicates the humidity of the air caused by both HP and water vapor
(2) Run terminated early
(3) No masks inside The above-described hydrogen peroxide sterilization device 10 provides several advantages. For example, the hydrogen peroxide pouch 14 can be sized to fit a large variety of enclosures and to accommodate a large range of sterilization loads. Only a small quantity of hydrogen peroxide is needed for individual medical device sterilization, making the hydrogen peroxide sterilization device 10 safe to use without training. Hydrogen peroxide concentrations can be adjusted to optimize sterilization and safety. More than one hydrogen peroxide membrane pouch can be used for large enclosures. The hydrogen peroxide pouch 14 may be reusable depending on the hydrogen peroxide concentration and active diffusion time. In some embodiments, the hydrogen peroxide pouch 14 is resealable. Off-the-shelf hermetic outer containers such as polyethylene bags or pails can be used.

Figure 2:
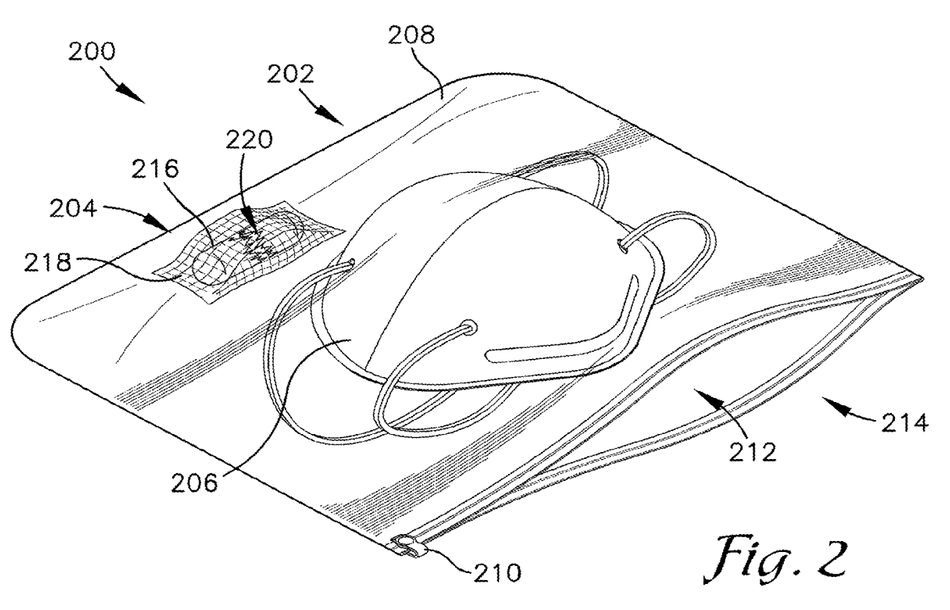
FIG. 2 is a perspective view of a hydrogen peroxide sterilization device constructed in accordance with another embodiment of the invention.

Turning to FIG. 2, a hydrogen peroxide sterilization device 200 constructed in accordance with another embodiment of the invention broadly comprises a hermetic outer container 202 and a hydrogen peroxide ampoule 204. The hydrogen peroxide sterilization device 200 is shown sterilizing an exemplary medical device 206, which may be a face mask or any other medical tool or personal health device. The hydrogen peroxide sterilization device 200 may also include an indicator and a desiccant pouch as described above.

The hermetic outer container 202 includes an outer wall 208 and an opening sealing mechanism 210. The hermetic outer container 202 may be molded to fit the item being sterilized (similar to clamshell packaging) to reduce the amount of hydrogen peroxide vapor required to fill the space around the item. The hermetic outer container 202 may be a polyethylene bag, a polypropylene bag, or any other suitable hermetic container. High density polyethylene provides an acceptable vapor barrier, whereas low density polyethylene may be a poor barrier to oxygen and hydrogen peroxide.

The outer wall 208 forms a sterilization enclosure 212 having an opening 214 and retains water vapor and hydrogen peroxide vapor in the sterilization enclosure 212. To that end, the outer wall 208 may be polyethylene, polypropylene, or any other suitable hermetic material. The outer wall 208 may be transparent, thus allowing a user to observe the medical device 206 or personal health device without opening the hermetic outer container 202. The outer wall 208 may be flexible for altering a volume of the sterilization enclosure 212.

The sterilization enclosure 212 receives the medical device 206 and the hydrogen peroxide ampoule 204 therein. The sterilization enclosure 212 may be approximately one liter in maximum volume or any other suitable size.

The opening 214 allows the user to insert the medical device 206 or personal health device and the hydrogen peroxide ampoule 204 into the sterilization enclosure 212. The opening 214 may be closed via the opening sealing mechanism 210.

The opening sealing mechanism 210 is configured to be selectively opened for inserting the medical device 206 or personal health device into and removing the medical device 206 or personal health device from the sterilization enclosure 212. The opening sealing mechanism 210 seals the sterilization enclosure 212 when the opening sealing mechanism 210 is closed. The opening sealing mechanism 210 may be a zip-to-close mechanism, a press-and-seal mechanism, or any other suitable hermetic sealing mechanism.

The hydrogen peroxide ampoule 204 comprises a glass tube 216 and a permeable membrane 218 and forms a solution chamber 220. The hydrogen peroxide ampoule 204 is configured to be inserted into the sterilization enclosure 212 with the medical device 206. The hydrogen peroxide ampoule 204 may provide longer hydrogen peroxide shelf life.

The glass tube 216 is a hermetic vessel that encloses the solution chamber 220 and hence retains hydrogen peroxide solution in the solution chamber 220. The glass tube 216 may be shattered, broken, crushed, punctured, or snapped (without puncturing the permeable membrane 218), when sterilization is desired.

The permeable membrane 218 encloses the glass tube 216 and may be a plastic sleeve with open or permeable ends, spun bonded polyethylene, such as Tyvek brand, or any other porous material, such as Gore-Tex brand, configured to allow hydrogen peroxide vapor to diffuse into the sterilization enclosure 212. The permeable membrane 218 may be heat sealed. The permeable membrane 218 may be transparent, thus allowing a user to observe an amount of hydrogen peroxide solution in the glass tube 216.

The hydrogen peroxide solution may be a mixture of water and hydrogen peroxide, such as the hydrogen peroxide solution supplied by Sigma Aldrich. Hydrogen peroxide concentration may be between 1% and 100% (pure hydrogen peroxide with no water). In one embodiment, inhibited hydrogen peroxide may be ACS reagent grade, between 10% and 35% (by weight). In another embodiment, ACS reagent grade, 30% (by weight) hydrogen peroxide solution may be used. The hydrogen peroxide solution may be between approximately 100 milliliters to approximately 500 milliliters.

Use of the hydrogen peroxide sterilization device 200 will now be described. First, the medical device 206 may be placed in the sterilization enclosure 212 of the hermetic outer container 202 via its opening 214. The hydrogen peroxide ampoule 204 may then be placed in the sterilization enclosure 212 with the medical device 100. The opening sealing mechanism 210 may then be closed so that no vapor can diffuse out of the sterilization enclosure 212. The glass tube 216 of the hydrogen peroxide ampoule 204 may then be shattered or broken.

At least some of the hydrogen peroxide in the hydrogen peroxide solution will then diffuse through the permeable membrane 218 in the form of vapor into the sterilization enclosure 212 and sterilize the medical device 206. To that end, the medical device 206 and the hydrogen peroxide ampoule 204 may be retained in the sterilization enclosure 212 for a predetermined or recommended amount of time, until the medical device 206 is needed again, or until the hydrogen peroxide solution has completely diffused into the sterilization enclosure 212

The opening sealing mechanism 210 may then be opened, and the medical device 206 may then be removed from the hermetic outer container 202. The hydrogen peroxide ampoule 204 may then be discarded.

Figure 3:
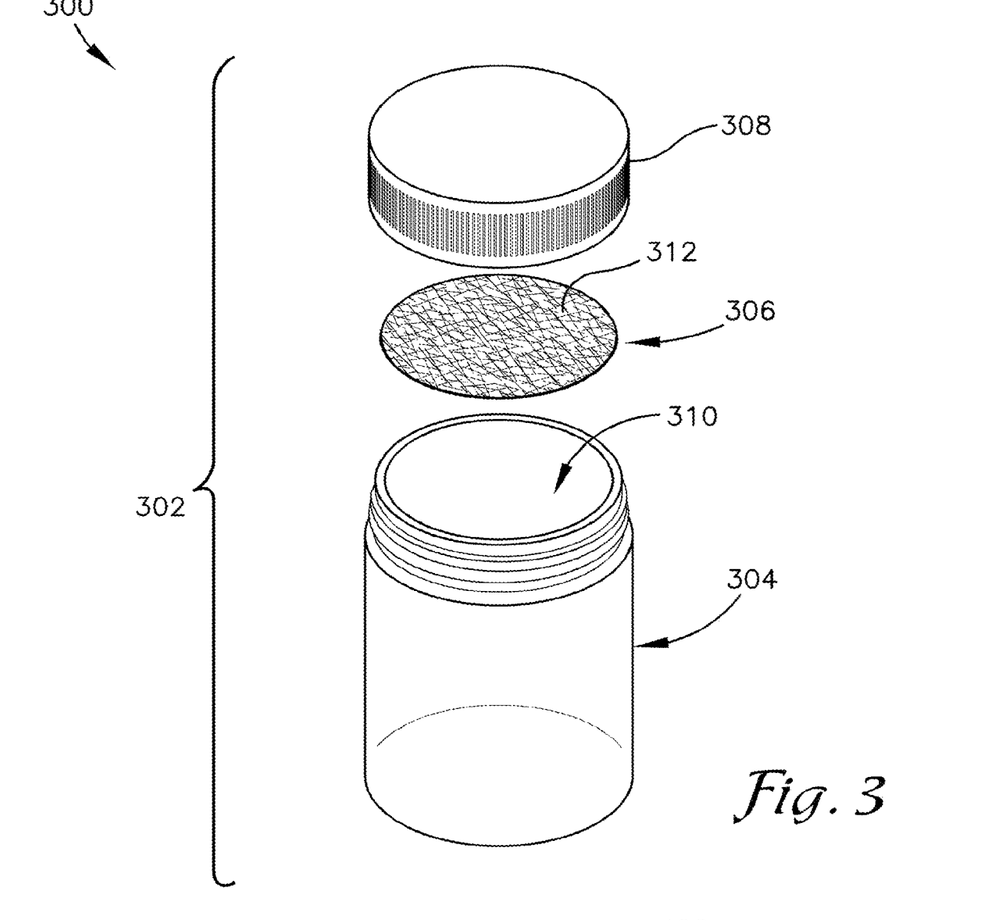
FIG. 3 is a receptacle of a hydrogen peroxide sterilization device constructed in accordance with another embodiment of the invention.

Turning to FIG. 3, a hydrogen peroxide sterilization device 300 constructed in accordance with another embodiment of the invention broadly comprises a hermetic outer container and a hydrogen peroxide receptacle 302. The hermetic outer container is substantially similar to the hermetic outer containers described above and will not be described further.

The hydrogen peroxide receptacle 302 includes a hermetic base vessel 304, a permeable lid 306, and a hermetic lid 308. The hydrogen peroxide receptacle 302 may be a closable bottle, a vile, a capsule, or any other suitable rigid receptacle.

The hermetic base vessel 304 may be a rigid or minimally flexible container forming a solution chamber 310. The hermetic base vessel 304 may be made of plastic, glass, ceramic, metal, or the like. The hermetic base vessel 304 may be transparent, thus allowing a user to observe an amount of hydrogen peroxide solution in the hydrogen peroxide receptacle 302. In one embodiment, the hermetic base vessel 304 also includes an indicator (e.g., a specific gravity indicator sphere) configured to identify a concentration or amount of hydrogen peroxide in the solution chamber 310.

The permeable lid 306 may include a permeable membrane 312 and is configured to be removably secured onto the hermetic base vessel 304 to fully enclose the solution chamber 310. To that end, the permeable lid 306 may be snapped or crimped onto the hermetic base vessel 304 or attached to the hermetic base vessel 304 via a fastener. Alternatively, the permeable lid 306 (and/or hermetic base vessel 304) may include helical threads for screwing the permeable lid 306 on to the hermetic base vessel 304.

The permeable membrane 312 may be spun bonded polyethylene, such as Tyvek brand or, any other porous material, such as Gore-Tex brand, configured to allow hydrogen peroxide vapor to diffuse out of the solution chamber 310. If the hermetic base vessel 304 is polyethylene, polypropylene or other thermoplastic the permeable membrane 312 may be heat sealed.

The hermetic lid 308 is configured to be removably secured onto the permeable lid 306 or onto the hermetic base vessel 304 over the permeable lid 306. To that end, the hermetic lid 306 may be snapped or crimped onto the permeable lid 306 or hermetic base vessel or attached to the permeable lid 306 or hermetic base vessel 304 via a fastener. Alternatively, the hermetic lid 308 may include helical threads for screwing the hermetic lid 308 onto the permeable lid 306 or hermetic base vessel 304. In one embodiment, the hermetic base vessel 304 may ship with the hermetic lid 308 and when ready for use, the permeable lid 306 is secured to the hermetic base vessel 304 with the hermetic lid 308.

Figure 4:
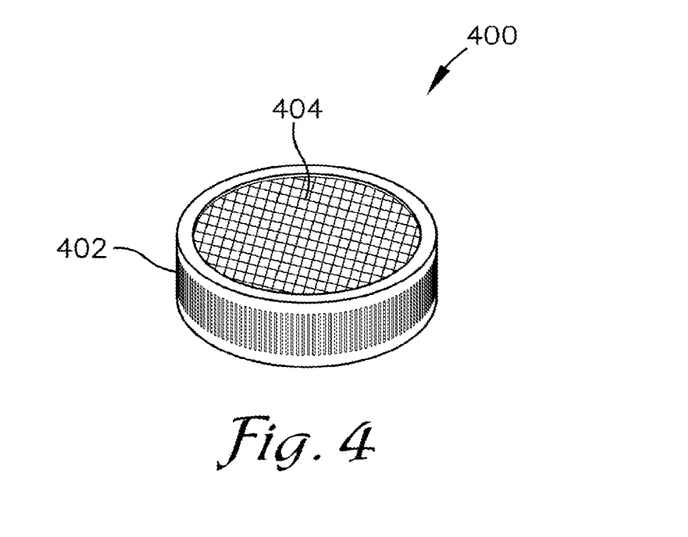
FIG. 4 is an alternative lid for use with the hydrogen peroxide sterilization device of FIG. 3.

Alternatively, as shown in FIG. 4, a permeable lid 400 including a securement rim 402 and a permeable membrane 404 may be used with the hermetic base vessel 304. The securement rim 402 and permeable membrane 404 may be a single component. For example, the securement rim 402 may be polypropylene with the permeable membrane 402 being fused to the securement rim 402.

Use of the hydrogen peroxide sterilization device 300 will now be described. A medical device may be placed in the sterilization enclosure of the hermetic outer container via its opening. The hermetic lid 308 and the permeable lid 306 may then be removed from the hermetic base vessel 304. A hydrogen peroxide solution may then be poured into the hermetic base vessel 304. The permeable lid 306 may then be secured onto the hermetic base vessel 304, thus sealing the hydrogen peroxide solution in the solution chamber 310. The hydrogen peroxide receptacle 302 may then be placed in the sterilization enclosure with the medical device. The opening sealing mechanism of the hermetic outer container may then be closed so that no vapor can diffuse out of the sterilization enclosure. In one embodiment, a dry gas may be added to the sterilization enclosure before it is closed to increase the diffusion of hydrogen peroxide vapor through the permeable membrane 312.

At least some of the hydrogen peroxide in the hydrogen peroxide solution will then diffuse through the permeable membrane 312 in the form of vapor into the sterilization enclosure and sterilize the medical device. To that end, the medical device and the hydrogen peroxide receptacle 302 may be retained in the sterilization enclosure for a predetermined or recommended amount of time (depending on the medical device or its application), until the medical device is needed again, until the hydrogen peroxide solution has completely diffused into the sterilization enclosure, or until the indicator indicates a particular amount of hydrogen peroxide solution has diffused into the sterilization enclosure.

The opening sealing mechanism may then be opened, and the medical device may then be removed from the hermetic outer container. The hydrogen peroxide receptacle 302 may be discarded, refilled and resealed (i.e., the hermetic lid 308 may be secured over the permeable lid or replaced if in case of threaded solution chamber 310) for future use, or reused if some of the hydrogen peroxide solution 34 remains. To that end, the hydrogen peroxide receptacle 302 may be stored in the hermetic outer container until the hydrogen peroxide sterilization device 300 is used again.

The above-described hydrogen peroxide sterilization device 300 provides several advantages in addition to the advantages described above. For example, the hydrogen peroxide receptacle 302 can be sized to fit a large variety of enclosures and to accommodate a large range of sterilization loads. The hydrogen peroxide receptacle 302 is easy to refill and can be safely stored in a portable first aid kit or medical cart. The permeable lid 306 and hermetic lid 308 allow the hydrogen peroxide receptacle 302 to be stored, used, and refilled by removing or securing the permeable lid 306 and/or the hermetic lid 308. To that point, no liner tearing, cutting, or puncturing is required, which is difficult for frail users and could lead to user injury.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

The invention claimed is:

1. A hydrogen peroxide sterilization device for sterilizing a medical device, the hydrogen peroxide sterilization device comprising:
- a hermetic outer container having a sterilization enclosure configured to receive the medical device;
- a hydrogen peroxide ampoule comprising a glass tube enclosing a solution chamber at least partially filled with a hydrogen peroxide solution, the hydrogen peroxide ampoule being configured to be positioned in the sterilization enclosure of the outer container,
- the glass tube being configured to be broken to allow hydrogen peroxide vapor to diffuse from the solution chamber into the sterilization enclosure; and
- a desiccant pouch positioned in the sterilization enclosure, the desiccant pouch including activated molecular sieves configured to reduce humidity in the sterilization enclosure.

2. The hydrogen peroxide sterilization device of claim 1, the hydrogen peroxide ampoule further comprising a permeable membrane enclosing the glass tube.

3. The hydrogen peroxide sterilization device of claim 2, wherein the permeable membrane is formed of spun bonded polyethylene, polypropylene, or porous fluoropolymer (Gore-Tex).

4. The hydrogen peroxide sterilization device of claim 2, wherein the permeable membrane is transparent.

5. The hydrogen peroxide sterilization device of claim 2, further comprising a dry gas in the sterilization enclosure to promote diffusion of the hydrogen peroxide through the permeable membrane.

6. The hydrogen peroxide sterilization device of claim 1, wherein the hermetic outer container is a high density polyethylene, perfluoroalkoxy alkanes (PFA), fluorinated ethylene propylene (FEP), metalized polyethylene terephthalate (Mylar), or metal.

7. The hydrogen peroxide sterilization device of claim 1, further comprising an indicator configured to identify a current concentration or amount of hydrogen peroxide in the solution chamber.

8. The hydrogen peroxide sterilization device of claim 1, the desiccant pouch further including a permeable membrane and a hermetic outer liner enclosing the permeable membrane, the hermetic outer liner being configured to prevent the activated molecular sieves from absorbing water out of the sterilization enclosure unless the hermetic outer liner is compromised.

9. The hydrogen peroxide sterilization device of claim 8, the hermetic outer liner being a plastic-lined metal pouch.

10. The hydrogen peroxide sterilization device of claim 1, the hermetic outer container having a molded shape.

11. The hydrogen peroxide sterilization device of claim 1, the hermetic outer container having a transparent outer wall.

12. The hydrogen peroxide sterilization device of claim 1, the hermetic outer container having a flexible outer wall for altering a volume of the sterilization enclosure.

\* \* \* \* \*